(12) United States Patent
Arba Mosquera et al.

(10) Patent No.: US 12,357,386 B2
(45) Date of Patent: Jul. 15, 2025

(54) METHOD FOR PROVIDING CONTROL DATA FOR AN EYE SURGICAL LASER OF A TREATMENT APPARATUS

(71) Applicant: SCHWIND eye-tech-solutions GmbH, Kleinostheim (DE)

(72) Inventors: Samuel Arba Mosquera, Aschaffenburg (DE); Anita Grimm, Eichenbühl (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 358 days.

(21) Appl. No.: 17/679,699

(22) Filed: Feb. 24, 2022

(65) Prior Publication Data

US 2022/0280241 A1 Sep. 8, 2022

(30) Foreign Application Priority Data

Mar. 8, 2021 (DE) ...................... 10 2021 105 543.1

(51) Int. Cl.
*A61B 34/10* (2016.01)
*A61B 18/00* (2006.01)
(Continued)

(52) U.S. Cl.
CPC ................ *A61B 34/10* (2016.02); *A61D 1/00* (2013.01); *A61F 9/00802* (2013.01);
(Continued)

(58) Field of Classification Search
CPC .......... A61B 34/10; A61B 2018/00678; A61B 2018/00714; A61B 2018/00761;
(Continued)

(56) References Cited

U.S. PATENT DOCUMENTS 6,129,723 A * 10/2000 Anderson ............ A61C 1/0046
606/17
6,964,659 B2 * 11/2005 Gross .................. A61F 9/00806
606/4
(Continued)

FOREIGN PATENT DOCUMENTS

EP 1 649 843 A1 4/2006

*Primary Examiner* — Jonathan T Kuo
(74) *Attorney, Agent, or Firm* — MEDLER FERRO WOODHOUSE & MILLS PLLC

(57) ABSTRACT

A method is disclosed for providing control data for an eye surgical laser of a treatment apparatus for the removal of tissue from a human or animal cornea. The method includes ascertaining a temperature distribution expected in the cornea per laser pulse, and determining, by using a temperature model of the cornea, a laser pulse sequence of a preset laser pulse distribution for removing the tissue. A respective laser pulse position in the cornea is preset by the laser pulse distribution and sequence. A temperature profile of the cornea is calculated by means of cumulated temperature distributions of the laser pulses in the temperature model and a difference profile to a preset limit temperature profile is determined. An order of the laser pulses is ascertained depending on the difference profile for determining the laser pulse sequence, and providing control data for controlling the laser pulse sequence for removing tissue.

14 Claims, 2 Drawing Sheets

(51) Int. Cl.
*A61D 1/00* (2006.01)
*A61F 9/008* (2006.01)

(52) U.S. Cl.
CPC .............. *A61F 9/00825* (2013.01); *A61B 2018/00678* (2013.01); *A61B 2018/00714* (2013.01); *A61B 2018/00761* (2013.01); *A61B 2034/104* (2016.02); *A61F 2009/00872* (2013.01); *A61F 2009/00878* (2013.01)

(58) Field of Classification Search
CPC ........ A61B 2034/104; A61B 2034/105; A61B 18/20–18/28; A61D 1/00; A61F 9/008–2009/00897
See application file for complete search history.

(56) References Cited

U.S. PATENT DOCUMENTS

| | | | |
|---|---|---|---|
| 8,603,081 B2* | 12/2013 | Berry | A61F 9/008 606/4 |
| 11,154,424 B2* | 10/2021 | Schuele | B29D 11/00461 |
| 2004/0111083 A1* | 6/2004 | Gross | A61F 9/00806 606/5 |
| 2009/0054879 A1* | 2/2009 | Berry | A61F 9/008 606/5 |
| 2012/0150160 A1* | 6/2012 | Vogler | A61F 9/00836 606/4 |
| 2018/0200532 A1* | 7/2018 | Luttrull | A61N 5/045 |
| 2019/0110921 A1 | 4/2019 | Wittnebel | |
| 2019/0307554 A1* | 10/2019 | Schuele | G02C 7/022 |

* cited by examiner

METHOD FOR PROVIDING CONTROL DATA FOR AN EYE SURGICAL LASER OF A TREATMENT APPARATUS

FIELD

The present invention relates to a method for providing control data for an eye surgical laser of a treatment apparatus for the removal of a tissue from a human or animal cornea. In addition, the invention relates to a treatment apparatus with at least one eye surgical laser and at least one control device for performing the method, to a computer program and to a computer-readable medium.

BACKGROUND

Treatment apparatuses and methods for controlling ophthalmological lasers for correcting an optical visual disorder and/or pathologically and/or unnaturally altered areas of the cornea are known in the prior art. Therein, a pulsed laser and a beam focusing device can for example be formed such that laser pulses effect a photodisruption and/or photoablation in a focus located within the organic tissue to remove a tissue, in particular a tissue lenticule, from the cornea. Control data of the laser for removing the tissue can preferably comprise a laser pulse distribution, which indicates, at which positions (laser pulse positions) in the cornea the individual laser pulses are to be placed ("spot build"), and a laser pulse sequence, which indicates the order, in which the laser pulse positions of the cornea are to be irradiated ("spot sequence"). Therein, the laser pulse sequence is preferably selected such that the laser pulse positions of the laser pulse distribution are processed as fast as possible to shorten a treatment duration and thereby an uncomfortable situation for a patient.

Therein, it is problematic that each laser pulse heats the tissue and a limit temperature of the tissue, at which the tissue denatures, can be reached with a too fast treatment. For example, collagens begin to denature from 40 degrees Celsius. Such a denaturation could result in problems in the treatment and/or a healing process and therefore is to be avoided.

From EP 1 649 843 A1, a photoablative laser with controllable pulse emission frequency is known. Therein, an average radiation frequency of the laser pulses is controlled as a function of respective areas of layers by a control device such that a target volume receives a number of laser pulses per time unit and per area unit below a predetermined threshold value in removing the layers.

SUMMARY

The invention is based on the object to provide improved control data for controlling an eye surgical laser.

This object is solved by the method according to the invention, the apparatuses according to the invention, the computer program according to the invention as well as the computer-readable medium according to the invention. Advantageous configurations with convenient developments of the invention are specified in the respective dependent claims, wherein advantageous configurations of the method are to be regarded as advantageous configurations of the treatment apparatus, of the control device, of the computer program and of the computer-readable medium and vice versa.

A first aspect of the invention relates to a method for providing control data for an eye surgical laser of a treatment apparatus for the removal of a tissue from a human or animal cornea, wherein the method comprises the following steps performed by a control device. Therein, an appliance, an appliance component or an appliance group is understood by a control device, which is configured for receiving and evaluating signals as well as for providing, for example generating, control data. The control device can for example be configured as a control chip, computer program, computer program product or control unit. Ascertaining a temperature distribution, which is expected in the cornea per laser pulse, is effected by the control device. Further, determining a laser pulse sequence of a preset laser pulse distribution for removing the tissue is effected by means of a temperature model of the cornea, wherein a respective laser pulse position in the cornea is preset by the laser pulse distribution and wherein it is preset by the laser pulse sequence, in which order the preset laser pulse positions are irradiated with the respective laser pulses, wherein a temperature profile of the cornea is calculated by means of cumulated temperature distributions of the laser pulses in the temperature model and a difference profile to a preset limit temperature profile is determined, wherein the order of the laser pulses is ascertained depending on the difference profile for determining the laser pulse sequence. Finally, providing control data for controlling the eye surgical laser, which uses the laser pulse sequence for removing the tissue, is effected.

In other words, control data is provided, in which the laser pulse sequence can be optimized based on the estimated temperature of the cornea. This means that an optimized laser pulse sequence, by which the cornea can be fastest and/or most gently treated, can be determined from the cumulated temperature distribution of the laser pulses, which can be provided as a temperature profile of the cornea. In particular, a laser pulse distribution can be preset to the effect, at which location of the cornea how many laser pulses have to be radiated to correct an optical visual disorder. The laser pulse sequence defines, in which order the laser pulse positions preset by the laser pulse distribution are irradiated. That is, it is indicated by the laser pulse sequence, at which point of time in an order of laser pulses a respective laser pulse position is selected. Thus, the laser pulse distribution represents the division of a volume of the cornea into laser pulse positions ("spot build") and the laser pulse sequence represents the order, in which the respective laser pulse positions are selected ("pulse list" or "spot sequence").

In order to determine the temperature profile of the cornea by means of the temperature model as accurately as possible, it can first be estimated, by which temperature an area of the cornea heats by a laser pulse, that is which temperature distribution arises per laser pulse. For example, this can be performed by means of a known absorption coefficient of the cornea and predetermined parameters of the laser pulse. For example, an energy and intensity of the laser pulse can be predetermined. Subsequently, it can be determined in the temperature model, how high the cumulated temperature distribution of the laser pulses for example is to be expected at a preset laser pulse sequence, wherein the temperature profile of the cornea arises from it. Therein, the temperature profile can be a digital representation of the cornea, which provides the temperature for each (volume) area of the cornea. This temperature distribution can be compared to a limit temperature profile, wherein for example a maximum temperature can be indicated in the limit temperature profile, which is allowed to occur in the cornea. In particular, a limit temperature, at which a tissue of the cornea denatures, can be indicated by the limit temperature profile. For example, a denaturation temperature of proteins can be indicated as the limit temperature, for example 40° C. Preferably, this limit temperature profile must not be exceeded, wherein a difference profile can be created from the calculated temperature profile and the limit temperature profile, by which the temperature difference at each laser pulse position in the cornea can be provided. Thus, it can for example be recognized, which laser pulse positions are still sufficiently far away from the limit temperature with their temperature. Thus, the laser pulse sequence can be selected such that the laser pulses are planned at those laser pulse positions, at which the difference profile is still sufficiently far away from the limit temperature profile. Preferably, this step can be performed as an optimization method. This means that the laser pulse sequence can be searched, in which a fastest and/or most temperature-friendly order of the laser pulses can be found. Herein, the temperature model and thereby the difference profile is preferably updated after each planned laser pulse such that the laser pulse sequence can be iteratively created, and the most optimum laser pulse position can be selected for each laser pulse. Subsequently, the laser pulse sequence thus ascertained can be provided in control data for controlling the eye surgical laser.

The temperature model of the cornea, by means of which the temperature profile can be determined, can be a physical or mathematical model, which is for example recorded in the control device. Preferably, determining the laser pulse sequence by means of the temperature model can be performed as a simulation before the actual treatment in that preset and/or predetermined parameters are provided to the temperature model, by means of which the temperature profile can be calculated.

The advantage arises by the invention that a safety in the treatment with the treatment apparatus can be improved since maximally admissible temperature limits can be complied with in improved manner. Furthermore, by the optimization of the laser pulse sequence, it can be achieved that a fastest possible treatment with as few treatment breaks as possible for cooling the cornea can be achieved. By shortening the treatment time, thus, cost can be saved, and a patient comfort can be increased.

The invention also includes forms of configuration, by which additional advantages arise.

A form of configuration provides that a cooling model of the cornea is further used in the temperature model for calculating the temperature profile, wherein a cooling of the cornea, in particular of the temperature profile of the cornea, over time is modeled by the cooling model. In other words, the temperature model cannot only include, how severely the cornea heats by a laser pulse, but also how the cornea cools over time. Herein, the temperature model can provide a calculation, which considers a temperature dissipation to an environment. Preferably, an ambient temperature can be preset for this calculation. For calculation, a diffusion model can for example be assumed, which describes a heat loss of the cornea as proportional to a difference of temperatures between the cornea and the environment. Preferably, the cooling of the cornea can be described by the cooling model in the form of an exponential function, which has a preset thermal relaxation time, with which the cornea can cool over time. By this form of configuration, the advantage arises that the cooling of the cornea can also be taken into account in the temperature model, whereby the laser pulse sequence can be even better optimized since the difference profile changes over time and thus laser pulse positions can again be irradiated, which were previously on the limit temperature profile.

In a further form of configuration, it is provided that a temperature spreading model of the cornea is further used in the temperature model for calculating the temperature profile, wherein a spreading of the temperature across the cornea depending on the time is modeled by the temperature spreading model. In other words, a temperature distribution, which a laser pulse generates in the cornea, can spread or distribute in the cornea over time. Thus, heat usually spreads from warm areas to cold areas of an object, that means that the temperature is averaged over the object. A heat conduction coefficient of the cornea can preferably be provided for this calculation. By this form of configuration, the advantage arises that the temperature model can even better describe a temperature profile of the cornea and thus the determination of the laser pulse sequence can be improved.

In a further form of configuration, it is provided that an angle of incidence model of the laser pulse on the cornea is further used in the temperature model for calculating the temperature profile, wherein the temperature distribution of the laser pulse depending on an angle of incidence of the laser pulse on the cornea is modeled by the angle of incidence model. In other words, it is taken into account, at which angle of incidence the laser pulse impinges on the cornea, which changes the temperature distribution for each laser pulse. In particular, the cornea can be curved, and the laser pulses do not all perpendicularly enter the tissue of the cornea. Thus, a different temperature distribution can arise for each laser pulse. In particular, a laser pulse can split into an absorbing portion in the cornea and a reflecting portion, wherein the reflecting and absorbing portions can vary with the angle of incidence on the cornea. Thus, an efficiency and thereby a temperature output of a laser pulse can reduce from a center to the outside, mainly due to an increase of the laser spot upon impingement on the cornea. Preferably, the angle of incidence model can be derived from the Lambert-Beer law, which describes an attenuation of an intensity of a radiation with respect to the initial intensity thereof upon passage through a medium (the cornea). By this form of configuration, the advantage arises that the temperature profile can be determined in improved manner, whereby a more accurate laser pulse sequence can be determined.

Preferably, it is provided that the temperature distribution per laser pulse is performed at least depending on a laser pulse intensity and a laser pulse wavelength. That means that for determining the temperature distribution, at least the laser pulse wavelength and thereby an energy and additionally the intensity are used to determine how the temperature profile changes upon impingement of a laser pulse on the cornea. Herein, it can for example be predetermined via experiments or simulations, how a temperature distribution presents itself depending on the laser pulse intensity and the laser pulse wavelength.

In a further form of configuration, it is provided that for determining the laser pulse sequence, the respective laser pulses are planned at the laser pulse position of the cornea, at which the difference profile has a preset minimum distance to the limit temperature profile at the point of time of radiation of the respective laser pulse. In other words, it can be calculated how the difference profile looks like at the point of time of the radiation of the respective laser pulse, wherein the respective laser pulse is planned at the laser pulse position of the cornea, at which the difference profile still has a preset minimum distance to the limit temperature profile. The preset minimum distance can include a safety value such that the limit temperature of the cornea, for example a temperature, at which proteins denature, is not reached by the subsequent laser pulse. Thus, all of the laser pulse positions can for example be examined for the presence of the preset minimum distance to the limit temperature profile before planning the laser pulse, wherein the laser pulse is planned at the laser pulse position, which complies with the preset minimum distance. If multiple laser pulse positions have the preset minimum distance, thus, the laser pulse can for example be randomly planned at one of these positions or the laser pulse can be planned at that laser pulse position, which has the largest distance between the difference profile and the limit temperature profile. By this form of configuration, a preferred determination of the laser pulse sequence can be achieved.

Preferably, it is provided that the cornea is divided into areas, wherein the laser pulses are positioned in one of the areas until the temperature profile in this area reaches the limit temperature profile, wherein the area is then changed. In other words, the cornea can be divided into multiple areas, wherein each area can have a preset number of laser pulse positions. Subsequently, the laser pulses can be planned in one of these areas, and the temperature profile can be determined in this area by means of the temperature model. If it is determined that the temperature profile in this area reaches the limit temperature profile, a subsequent laser pulse can be planned in another area, wherein the other area can then be calculated with a maximum number of laser pulses until the limit temperature profile is reached before this is continued with the further areas. Thus, the laser pulse sequence for the entire cornea can be determined as fast as possible, wherein a first area, which has first reached the limit temperature profile, is preferably already cooled as far as it can again be irradiated after a complete passage of the areas of the cornea. Thus, the laser pulse sequence for the cornea can be particularly fast and securely provided.

In a further form of configuration, it is provided that for determining the laser pulse sequence, the respective laser pulses are planned at the laser pulse position of the cornea, at which the difference profile has a maximum difference between the temperature profile and the limit profile at the point of time of the radiation of the respective laser pulse. In other words, the laser pulse position is searched, which has a maximum difference between the temperature profile and the limit temperature profile. At this location, the radiation of the next laser pulse is then planned. This can be iteratively performed for all of the laser pulse positions until the entire laser pulse sequence is fixed. Thus, it can be ensured that always the safest laser pulse position is selected, wherein it is preferably ensured that the limit temperature profile is not exceeded.

In a further form of configuration, it is provided that, if it is determined that the limit temperature profile is reached in the cornea and/or in an area of the cornea, an irradiation break, in particular for the area of the cornea, is planned. In other words, irradiation breaks can be planned if all of the laser pulse positions have reached the limit temperature profile. Preferably, the duration of the irradiation break can be determined by the temperature model. This means that it can for example be calculated due to a known cooling when the cornea or the area of the cornea has cooled as far as further laser pulses can be emitted to the cornea. In particular, multiple irradiation breaks can also be planned, which are taken into account in planning the laser pulse sequence. By this form of configuration, a safety in the treatment with the treatment apparatus can be improved.

A second aspect of the present invention relates to a control device, which is configured to perform one of the above described methods. The above cited advantages arise. For example, the control device can be configured as a control chip, control unit or application program ("app"). The control device can preferably comprise a processor device and/or a data storage. An appliance or an appliance component for electronic data processing is understood by a processor device. The processor device can for example comprise at least one microcontroller and/or at least one microprocessor. Preferably, a program code for performing the method according to the invention can be stored on the optional data storage. The program code can then be configured, upon execution by the processor device, to cause the control device to perform one of the above described embodiments of one or both methods according to the invention.

A third aspect of the present invention relates to a treatment apparatus with at least one eye surgical laser for the separation of a tissue predefined by the control data, in particular of a corneal volume with predefined interfaces of a human or animal eye by means of photodisruption and/or photoablation, with at least one control device for the laser or lasers, which is formed to execute the steps of the method according to the first aspect of the invention. The treatment apparatus according to the invention allows that the disadvantages occurring in the use of usual ablative treatment apparatuses are reliably reduced or even avoided.

In a further advantageous configuration of the treatment apparatus according to the invention, the laser can be suitable to emit laser pulses in a wavelength range between 150 nm and 250 nm, preferably between 175 nm and 215 nm, at a respective pulse duration between 1 fs and 100 ns, preferably between 10 ps and 10 ns, and a repetition frequency of greater than 100 Hertz (Hz), preferably between 400 Hz and 10 kilohertz (MHz). Such an ablation laser, which can in particular be formed as an excimer laser, is particularly well suitable for ablation of tissue of the cornea. The use of lasers in a wavelength range below 300 nm, which is also referred to as "deep ultraviolet", can particularly efficiently ablate the tissue of the cornea by these very short-wavelength and high-energy beams. Photoablative lasers of the type used here usually input pulsed laser radiation with a pulse duration between 1 fs and 100 ns into the corneal tissue. In particular, the range between 175 nm and 215 nm can also be selected as the wavelength range.

In a further advantageous configuration of the treatment apparatus according to the invention, the laser can be suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kilohertz (kHz), preferably between 100 kHz and 100 megahertz (MHz). Such a femtosecond laser is particularly well suitable for removing tissue within the cornea. The use of photodisruptive and/or photoablative lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy is allowed in the generation of the interfaces. In particular, the range between 700 nm and 780 nm can also be selected as the wavelength range.

In further advantageous configurations of the treatment apparatus according to the invention, the control device can comprise at least one storage device for at least temporary storage of at least one control dataset, wherein the control dataset or datasets include(s) control data for positioning and/or for focusing individual laser pulses in the cornea; and can comprise at least one beam device for beam guidance and/or beam shaping and/or beam deflection and/or beam focusing of a laser beam of the laser. Therein, the mentioned control dataset includes the control data determined in the method for removing the tissue.

Further features and the advantages thereof can be taken from the descriptions of the first inventive aspect, wherein advantageous configurations of each inventive aspect are to be regarded as advantageous configurations of the respectively other inventive aspect.

A fourth aspect of the invention relates to a computer program including commands, which cause the treatment apparatus according to the fourth inventive aspect to execute the method steps according to the first inventive aspect and/or the method steps according to the second inventive aspect.

A fifth aspect of the invention relates to a computer-readable medium, on which the computer program according to the fourth inventive aspect is stored. Further features and the advantages thereof can be taken from the descriptions of the first to fourth inventive aspects, wherein advantageous configurations of each inventive aspect are to be regarded as advantageous configurations of the respectively other inventive aspect.

BRIEF DESCRIPTION OF DRAWINGS

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

In the figures, identical or functionally identical elements are provided with the same reference characters.

DETAILED DESCRIPTION

Figure 1:
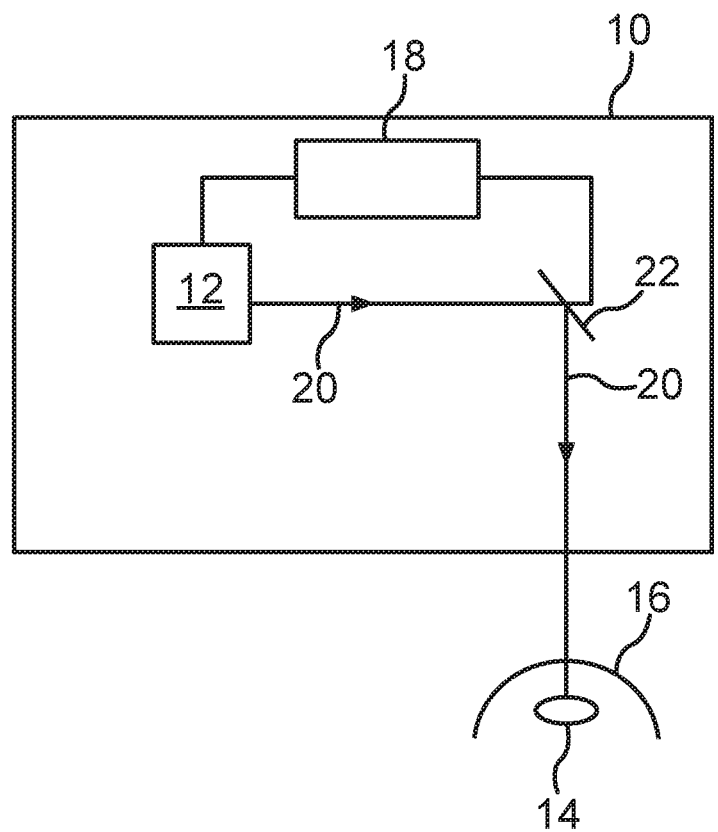
FIG. 1 is a schematic representation of a treatment apparatus according to the invention according to an exemplary embodiment.

FIG. 1 shows a schematic representation of a treatment apparatus 10 with an eye surgical laser 12 for the removal of a tissue 14 from a cornea of a human or animal eye 16 by means of photodisruption and/or photoablation. The tissue 14 can for example represent a lenticule or also volume body, which can be separated from a cornea of the eye 16 by the eye surgical laser 12 for correcting a visual disorder. A laser pulse sequence and a laser pulse distribution for removing the tissue 14 can be provided in the form of control data by a control device 18 such that the laser 12 emits pulsed laser pulses to laser pulse positions preset by the control data in an order preset by the control data to remove the tissue 14. Alternatively, the control device 18 can be a control device 18 external with respect to the treatment apparatus 10.

Furthermore, FIG. 1 shows that the laser beam 20 generated by the laser 12 can be deflected towards the eye 16 by means of a beam deflection device 22, namely a beam deflection device such as for example a rotation scanner, to remove the tissue 14. The beam deflection device 22 can also be controlled by the control device 18 to remove the tissue 14.

Preferably, the illustrated laser 12 can be a photodisruptive and/or photoablative laser, which is formed to emit laser pulses in a wavelength range between 300 nanometers and 1400 nanometers, preferably between 700 nanometers and 1200 nanometers, at a respective pulse duration between 1 femtosecond and 1 nanosecond, preferably between 10 femtoseconds and 10 picoseconds, and a repetition frequency of greater than 10 kilohertz, preferably between 100 kilohertz and 100 megahertz. Alternatively, the laser 12 can be formed to emit laser pulses in a wavelength range between 150 nm and 250 nm, preferably between 175 nm and 215 nm, at a respective pulse duration between 1 fs and 100 ns, preferably between 10 ps and 10 ns, and a repetition frequency of greater than 100 Hz, preferably between 400 Hz and 10 KHz.

In addition, the control device 18 optionally comprises a storage device (not illustrated) for at least temporary storage of at least one control dataset, wherein the control dataset or datasets include(s) control data for positioning and/or for focusing individual laser pulses in the cornea 16.

In a treatment with the treatment apparatus 10 shown in FIG. 1, a laser pulse distribution can be preset, which can be used for removing the tissue and presets the respective laser pulse position in the cornea. The laser pulse distribution can for example be determined from predetermined examination data, which is to correct an optical visual disorder of the eye 16. Upon radiation of the laser pulses 20 onto the cornea, however, the cornea is heated by each laser pulse since energy is deposited in the tissue. This is problematic in that the cornea can raise above a temperature limit value, which causes the tissue of the cornea to denature, over time in certain areas, which are irradiated by the laser pulses 20 in fast sequence. In particular, it is known that tissue of the cornea can denature from 40° C. Such a denaturation would result in a degradation of the treatment result and impede a healing process. Furthermore, optical artifacts could arise by denatured areas in the cornea.

In order that the cornea does not reach this temperature limit value, it can be provided to correspondingly adjust or vary the laser pulse sequence, with which the laser pulse positions are selected, such that not too many laser pulses are radiated to an area of the cornea in too short time. Herein, the suitable point of time for each laser pulse is preferably searched, by which the respective laser pulse positions are irradiated. Correspondingly, the laser pulses can then be sorted in the laser pulse sequence, wherein a difference in time between two laser pulses can preferably be preset by a laser pulse frequency.

Figure 2:
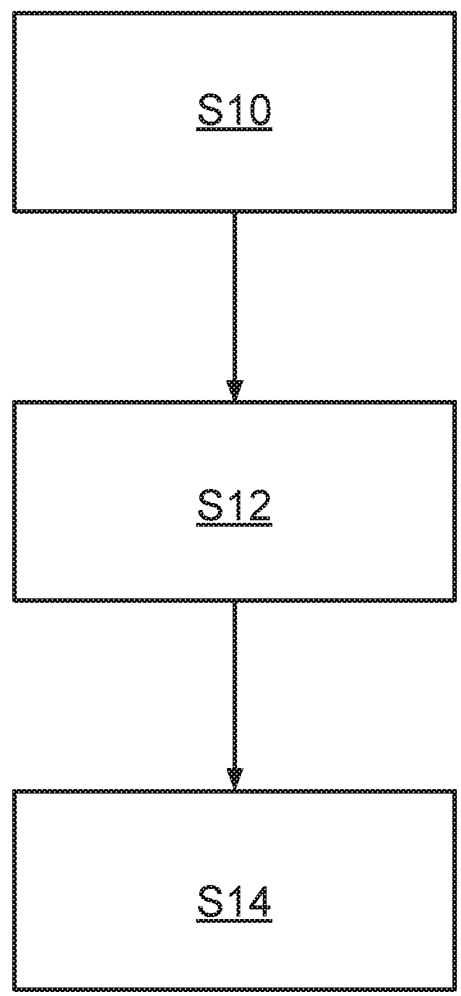
FIG. 2 is a schematic method diagram according to an exemplary embodiment.

In order to determine the laser pulse sequence and to provide it as control data for controlling the eye surgical laser, the method shown in FIG. 2 can be performed, preferably by the control device 18 of the treatment apparatus 10.

In a step S10, a temperature distribution can first be ascertained, which is expected in the cornea per laser pulse. This laser pulse distribution can for example be estimated by means of the formula $$\Delta T = \frac{\alpha}{\rho c} I(1 - R)$$

wherein ΔT represents the temperature difference, α represents an absorption coefficient of the cornea, ρ represents a density of the cornea, c represents a specific thermal capacity, R represents a reflectivity of the cornea and I represents a beam exposition. The beam exposition can in particular be determined depending on the laser pulse intensity and a used laser pulse wavelength by means of known approaches.

Subsequently, in a step S12, it can be determined, in particular in iterative manner and by means of a temperature model of the cornea, how a temperature profile of the cornea changes by means of cumulated temperature distributions of the individual laser pulses. The temperature profile can indicate a temperature for each position of the cornea, as it is expected upon irradiation with a preset number of laser pulses. For example, the temperature profile of the cornea can be calculated in a first approach in that an equally distributed laser pulse sequence is assumed. Furthermore, a difference profile can be calculated, which represents a difference of the temperature profile to a preset limit temperature profile. Herein, the limit temperature profile can represent the limit temperature for each position of the cornea. The difference profile can for example indicate in degrees Celsius, which temperature difference is still present between the estimated temperature profile and the limit temperature profile. Based on this difference profile, it can then be determined, in which position of the cornea there is still enough distance to the limit temperature profile, wherein the laser pulse sequence can then be planned based on this difference profile.

In order that the temperature model represents a modeling of the current situation in the cornea as accurate as possible, it can be provided that an angle of incidence model of the laser pulse on the cornea is also taken into account besides the cumulated temperature distribution, which arises by the laser pulses. In particular, not all of the laser pulses perpendicularly impinge on the cornea since it is curved and thus laser pulses can obliquely impinge on edge areas of the cornea. Thus, the reflectivity R and the absorption coefficient α can in particular deviate depending on the angle.

Furthermore, it can be taken into account that the cornea cools over time. Thus, a laser pulse position can dissipate heat to an environment over time such that even with a once reached limit temperature for a laser pulse position, the laser pulse position is cooled after a preset time as far as it can be again irradiated. Therefore, it is preferably provided that a cooling model of the cornea is further taken into account in the temperature model, in which the cooling of the cornea, in particular of the temperature profile of the cornea, is modeled over time. Preferably, this cooling model can be derived from the Newton's cooling law and be taken into account by means of $$T(t) = T_{env} + (T(0) - T_{env})e^{-\left(\frac{t}{\tau}\right)}$$

wherein T(t) denotes the temperature at the point of time t and $T_{env}$ is an ambient temperature of the treatment apparatus 10. In the exponent of the exponential function e, the constant τ denotes a thermal relaxation time, which can be preset for the cornea and which can be calculated by means of an absorption coefficient, a thermal conductivity, a density and a thermal capacity of the cornea.

Furthermore, it can preferably be provided in the temperature model that a temperature distribution generated by a laser pulse does not locally remain at a location, but spreads across the cornea over time. Therefore, it can preferably be provided that the temperature model additionally includes a temperature spreading model of the cornea, in which a spreading of the temperature, in particular of the temperature distribution of a laser pulse, over time is modeled. Hereto, the cornea can for example be assumed as a temperature matrix, wherein the temperature from a point in this temperature matrix can divide to its neighbors over time. In particular, it can be assumed that the temperature spreads over time by means of the formula $$\frac{\partial T}{\partial t} = k\left(\frac{\partial^2 T}{\partial x^2} + \frac{\partial^2 T}{\partial y^2} + \frac{\partial^2 T}{\partial z^2}\right)$$

into the spatial directions x, y and z, wherein k represents a temperature conductivity of the cornea.

By means of the temperature model, which can for example comprise one or more of the previously mentioned models, in particular the cooling model, the temperature spreading model and/or the angle of incidence model, the temperature profile of the cornea can be particularly accurately estimated after each laser pulse. In order that the laser pulses are sorted in a preferred order in the laser pulse sequence, in particular complying with the maximum temperature, it can be provided that a respective laser pulse is planned at the laser pulse position at the time, at which the difference profile has a preset minimum distance to the limit temperature profile at the point of time of the radiation of the respective laser pulse.

Thus, a first laser pulse in the laser pulse sequence can for example be arbitrarily planned at a laser pulse position in the cornea, and the temperature profile can be determined by means of the temperature model. After the first laser pulse, it is to be assumed that the temperature profile still has a preset minimum distance to the limit temperature profile over the entire cornea. Therefore, the subsequent laser pulse can be planned at a further arbitrary position of the cornea, for example at the same laser pulse position. This can be performed until it is determined that a preset minimum distance to the limit temperature profile is reached at one of the laser pulse positions. After this minimum distance is reached for this laser pulse position, a next laser pulse position can be selected until the minimum distance is reached for it too. Thus, the laser pulse sequence can be iteratively planned for each laser pulse position until the entire laser pulse distribution is processed. Preferably, a first laser pulse position, which has been irradiated and in which the minimum distance has been reached, can cool after some time such that the preset minimum distance is again complied with for the first laser pulse position and laser pulses can again be planned. The preset minimum distance can for example have a safety distance before reaching the limit temperature profile. For example, the preset minimum distance can be 0.1° C. to 2° C.

Particularly preferably, the cornea can be divided into areas, wherein the temperature profile can be monitored for reaching the limit temperature profile in the respective area, wherein the area is changed, if this is the case. It is meant with areas, that laser pulse positions preset in the laser pulse distribution can be defined into areas in clustered manner, wherein the sequence of the laser pulses is first placed in a first area, until it is determined that the limit temperature is reached in this area, whereupon the area can be changed. After a complete passage of the areas, the first area can have cooled as far as it can again be taken into account for planning laser pulses.

Alternatively, it can be provided that the laser pulse sequence is planned such that the subsequent laser pulse is planned at the laser pulse position in the cornea, at which the difference profile has a maximum difference between the temperature profile and the limit temperature profile. This means that it can be checked for a respective laser pulse, at which location the difference profile is maximum, wherein this laser pulse is then planned at this location. This can be iteratively performed for all of the laser pulses. Therein, it can preferably be observed that the preset minimum distance to the limit temperature profile is complied with.

If it is determined that the limit temperature profile, in particular the minimum distance to the limit temperature profile, is reached in all of the laser pulse positions of the laser pulse distribution, an irradiation break can be planned, until it is determined that the cornea or an area of the cornea is again below the preset minimum distance.

Thus, a safety in the treatment with the treatment apparatus 10 can overall be improved and an acceleration of the treatment can be achieved since the laser pulses can be optimally planned, in particular with regard to a heating of the cornea, and thus unnecessary irradiation breaks can be avoided.

What is claimed is:

1. A method for providing control data for an eye surgical laser of a treatment apparatus for the removal of a tissue from a human or animal cornea, wherein the method comprises the following steps performed by a control device:
    ascertaining a temperature distribution, which is expected in the cornea per laser pulse;
    determining a laser pulse sequence of a preset laser pulse distribution for removing the tissue by means of a temperature model of the cornea, wherein
        a respective laser pulse position in the cornea is preset by the laser pulse distribution and wherein it is preset by the laser pulse sequence, in which order the preset laser pulse positions are irradiated with the respective laser pulses,
        a temperature profile of the cornea is calculated by means of cumulated temperature distributions of the laser pulses in the temperature model and a difference profile to a preset limit temperature profile is determined, wherein the order of the laser pulse positions is ascertained depending on the difference profile for determining the laser pulse sequence; and
    providing control data for controlling the eye surgical laser, which uses the laser pulse sequence for removing the tissue;
    wherein for determining the laser pulse sequence, the respective laser pulses are planned at the laser pulse position of the cornea, at which the difference profile has a maximum difference between the temperature profile and the limit temperature profile at the point of time of the radiation of the respective laser pulse.

2. The method according to claim 1, wherein a cooling model of the cornea is further used in the temperature model for calculating the temperature profile, wherein a cooling of the cornea over time is modeled by the cooling model.

3. The method according to claim 1, wherein a temperature spreading model of the cornea is further used in the temperature model for calculating the temperature profile, wherein a spreading of the temperature across the cornea depending on the time is modeled by the temperature spreading model.

4. The method according to claim 1, wherein an angle of incidence model of the laser pulse on the cornea is further used in the temperature model for calculating the temperature profile, wherein the temperature distribution of the laser pulse depending on an angle of incidence of the laser pulse on the cornea is modeled by the angle of incidence model.

5. The method according to claim 1, wherein the temperature distribution per laser pulse is performed at least depending on a laser pulse intensity and a laser pulse wavelength.

6. The method according to claim 1, wherein for determining the laser pulse sequence, the respective laser pulses are planned at the laser pulse position of the cornea, at which the difference profile has a preset minimum distance to the limit temperature profile at the point of time of the radiation of the respective laser pulse.

7. The method according to claim 6, wherein the cornea is divided into areas, wherein the laser pulses are positioned in one of the areas until the temperature profile in this area reaches the limit temperature profile, wherein the area is then changed.

8. The method according to claim 1, wherein if it is determined that the limit temperature profile is reached in the cornea and/or an area of the cornea, an irradiation break is planned.

9. A control device, which is formed to perform a method according to claim 1.

10. A treatment apparatus with at least one eye surgical laser for the removal of a tissue of a human or animal eye by means of photodisruption and/or photoablation, and at least one control device according to claim 9.

11. The treatment apparatus according to claim 10, wherein the laser is formed to emit laser pulses in a wavelength range between 150 nm and 250 nm, at a respective pulse duration between 1 fs and 100 ns, and a repetition frequency of greater than 100 Hz.

12. The treatment apparatus according to claim 10, wherein the laser is formed to emit laser pulses in a wavelength range between 300 nm and 1400 nm, at a respective pulse duration between 1 fs and 1 ns, and a repetition frequency of greater than 10 KHz.

13. The treatment apparatus according to claim 10, wherein the control device
    comprises at least one storage device for at least temporary storage of at least one control dataset, wherein the control dataset or datasets include(s) control data for positioning and/or focusing individual laser pulses in the cornea; and
    includes at least one beam device for beam guidance and/or beam shaping and/or beam deflection and/or beam focusing of a laser beam of the laser.

14. A non-transitory computer-readable medium storing a computer program including commands, which cause the treatment apparatus according to claim 10 to execute a method for providing control data for an eye surgical laser of a treatment apparatus for the removal of a tissue from a human or animal cornea, wherein the method comprises the following steps performed by a control device:
- ascertaining a temperature distribution, which is expected in the cornea per laser pulse;
- determining a laser pulse sequence of a preset laser pulse distribution for removing the tissue by means of a temperature model of the cornea,
- wherein a respective laser pulse position in the cornea is preset by the laser pulse distribution and wherein it is preset by the laser pulse sequence, in which order the preset laser pulse positions are irradiated with the respective laser pulses,
- wherein a temperature profile of the cornea is calculated by means of cumulated temperature distributions of the laser pulses in the temperature model and a difference profile to a preset limit temperature profile is determined, and
- wherein the order of the laser pulse positions is ascertained depending on the difference profile for determining the laser pulse sequence; and
- providing control data for controlling the eye surgical laser, which uses the laser pulse sequence for removing the tissue.

* * * * *